(12) United States Patent
Zhou et al.

(10) Patent No.: US 6,245,813 B1
(45) Date of Patent: Jun. 12, 2001

(54) USE OF UBENIMEX AND THE PHARMACEUTICAL COMPOSITION CONTAINING IT FOR TREATING VIRUS HEPATITIS

(75) Inventors: Shanxue Zhou; Lin Ai; Ping Wang; Chuanhua Ye; Mingxiu Peng, all of Sichuan (CN)

(73) Assignee: Sichuan Industrial Institute of Antibiotics, Sichuan (CN)

( * ) Notice: Subject to any disclaimer, the term of this patent is extended or adjusted under 35 U.S.C. 154(b) by 0 days.

(21) Appl. No.: 08/973,958

(22) PCT Filed: Jun. 21, 1996

(86) PCT No.: PCT/CN96/00046

§ 371 Date: Mar. 19, 1998

§ 102(e) Date: Mar. 19, 1998

(87) PCT Pub. No.: WO97/00677

PCT Pub. Date: Jan. 9, 1997

(30) Foreign Application Priority Data

Jun. 21, 1995 (CN) .............................................. 95 1 07019

(51) Int. Cl.[7] .................................................... A01N 37/12

(52) U.S. Cl. .............................................................. 514/563

(58) Field of Search .............................................. 514/563

(56) References Cited

U.S. PATENT DOCUMENTS 4,308,256  12/1981  McGregor ............................ 424/177

FOREIGN PATENT DOCUMENTS

| 2528984 | 6/1976 | (DE) | ............................ A61K/31/195 |
| 60-9487 | 3/1985 | (JP) | ............................ A61K/31/195 |
| 62-72613 | 4/1987 | (JP) | ............................ A61K/31/195 |
| 4-193827 | 7/1992 | (JP) | ............................ A61K/31/195 |

OTHER PUBLICATIONS

Hahm et al, NS3–4A of Hepatitis C Virus is a Chymotrypsin–Like Protease, Journal of Virology, vol. 69(4), pp. 2534–2539, 1995.

*Primary Examiner*—Russell Travers
(74) *Attorney, Agent, or Firm*—Alston & Bird LLP

(57) ABSTRACT

The present invention relates to the use of Ubenimex or salts thereof and the pharmaceutical composition containing them for the treatment of virus hepatitis, espcially chronic hepatitis B.

15 Claims, No Drawings

USE OF UBENIMEX AND THE PHARMACEUTICAL COMPOSITION CONTAINING IT FOR TREATING VIRUS HEPATITIS

FIELD OF THE INVENTION

This invention is directed to the use of Ubenimex or the salt thereof and pharmaceutical composition comprising Ubenimex or the salt thereof for the treatment of viral Hepatitis.

BACKGROUND OF THE INVENTION

Viral Hepatitis is a worldwide infectious disease with great hazard to human health, and at least five pathogens of hepatitis virus have been found, i.e, HAV, HBV, HCV, HDV and HEV respectively. All of the 5 viruses can induce acute Hepatitis, which can progress to chronic hepatitis in the case of HBV, HCV and HDV infection. Acute Hepatitis has self-limited chracteristic and the patients with acute hepatitis can be healed completely, whereas the treatment of chronic Hapatitis is very difficult, in particular hepatitis B with high disease incidence. At present, over 280 million people are HBeAg carriers, among whom about 78 million suffer from Hepatitis B.

The following are current clinical agents mainly useful in the treatment chronic Hepatitis B.

1. anti-viral agents such as Interferon

Interferon is a relatively ideal anti-chronic Hepatitis B agent at present, and remission occurs in 30~45% of the IFN-treated patients, with HBeAg undetectable and the liver histologically improved. And 5~25% of the patients can be cured, negative for both HBeAg and HBsAg. However, incapable for oral administration and with comparatively high cost, INF therapy is not likely to be widely used, particularly among the non-hospitalized patients. Moreover, patients treated with Interferon are usually associated with sever side effects such as high fever, shivering, hypotention, nausea, diarrhea, myalgia, headache and lassitude. All these factors consist of great barrier for extensive use of INF.

2. other anti-viral agents such as Vidarabine, Vidarabine phosphate, Aciclovir, Forscarnet, Zidovudine, Suramin, Polycytidylic Acid, 2', 3'-dideoxyl cytidine.

Due to indefinite clinical efficacy and sever side effects, these agents are not put into general use.

3. Immunomodulant (1) Cytokines such as Thymosine, immune RNA, Transferfactors and Interleukin-2

(2) Hormone such as Adrenocortical hormone and Prostaglandin (3) Specific and non-specific antigen or specific antibody such as HB vaccine, BCG vaccine, Polysacchride from Mycobacterium graminis, and high potency Immunoglobulin (4) Compound effecting intercellular cyclic nucleotide such as imidazole agents.

However, these Immunomodulants are still studied in the stage of experimental research.

4. Chinese traditional medicine such as Polyporus umbellatus polysaccharose, aqueous injection with active ingredient from the root of subprostrate sophora, Matrine in injection form and Polylentinan whose herapeutic efficacy, however, remains to be furtherly verified.

Therefore, it is necessary for developing novel anti-viral Hepatitis agents with high efficacy, lower side effect and convenient administration.

DESCRIPTION OF THE INVENTION

This invention aims to develop an anti-viral Hepatitis agent with high efficacy and lower side effects.

After extensive and profound research, the inventor has unexpectedly found that Ubenimex and the salt thereof exhibits good efficacy against Hepatitis, particularly against chronic Hepatitis B, with significantly lower side effect. The present invention is finished on the basis of the above finding.

Ubenimex is a compound of the following formula,

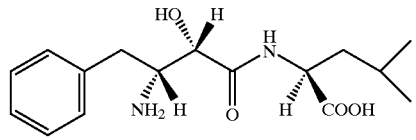

with the chemical name of N-[(2 S, 3 R)-3-amino-2-hydroxyl-4-phenyl butyryl]-Leucine. Firstly isolated from fermentation broth of Streptomyces olivoreticuli (Strain $MD_{976}$- $C_7$) by H. Umezawa, the compound demonstred siguificant inhibitory activity against aminopeptidase B and leucine aminopeptidase. [J. Antibiotics, 29, 97–99 (1976)].

In the present, Ubenimex is mainly used as anticancer agent (Jpn. JP 60–9487, Kokai Tokkyo Koho JP 4-193827), agent for relief of radiation side effects. Jpn. Kokai Tokkyo Kohl JP 3-110150), anti-thrombosis agent (Jpu. Kokai Tokky Koho JP 62-72613) and analgesic agent for nervous periphery (U.S. Pat. No. 4,308,256). However, no report has been found to involve its usage in viral Hepatitis treatment.

The present invention firstly relates to the use of Ubenimex and the salt thereof for the treatment of viral Hepatitis, especially for the treatment of chronic Hepatitis B, wherein the effective therapeutic amount of Ubenimex and the salt thereof is administered to the patient with viral Hepatitis, especially with chronic Hepatitis B.

Furthernore, the present invention relates to the use of the pharmaceutical composition comprising Ubenimex or the salt thereof for the treatment of patient with viral Hepatitis, particularly with chronic Hepatitis B, wherein the pharmaceutical composition comprise Ubenimex or the salt thereof, and the pharmaceutically acceptable adjuvant and excipient, with or without other anti-viral Hepatitis agents.

The present invention also relates to the use of Ubenimex or the salt thereof for the manufacture of anti-viral Hepatitis agent, which consist of the effective therapeutic amount of Ubenimex or the salt thereof, and pharmaceutically acceptable adjuvant and excipient, with or without other ant-viral Hepatitis agent.

According to the present invention, Ubenimex and the pharmaceutical composition comprising Ubenimex can be administered by various appropriate route, among which oral administration is preferred. The dosage for administration, depending on the age, sex, and weight of patient, degree of the liver infection, and administration route etc, is usually 10–100 mg per day.

The following examples of pharmacological study are given to illustrate the biological activity of Ubenimex against virul Hepatitis.

EXAMPLE 1

Material and Method

1. Animal Model:

as Ducklings of 1–2 days old incubated from healty Chongqing tamed ducks were inoculated with 0.1 ml of DHBV DNA positive serum by the abdominal cavity, and were bled through the vein in the neck 1 week after inoculation. Blot hybridization assay by Digoxigenin-labeled DHBV DNA probe was carried out to select the DHBV DNA positive ducklings as the experimental animals, which were raised for further one month.

2. Animal grouping and Drug Administraition

Seventy-six of the 1 month old ducks, positive of DHBV DNA, were randomly divided into 5 groups:

(1) negative control group: fasting administration of starch capsule by the oral route in the morning at a dose of 0.8 g/kg/day, once daily.

(2) positive control group: injected with Aciclovir by the abdominal cavity once daily, with the dosage of 100 mg/kg/day.

(3) Ubenimex group: low dose of 0.5 mg/kg/day.

(4) Ubenimex group: medium dose of 5 mg/kg/day.

(5) Ubenimex group: high dose of 25 mg/kg/day.

In group(3), (4) and (5), Ubenimex was available in the form of white powder, capsulized with starch. Fasting oral administration was undertaken every morning for 1 month.

3. Assay (1) serum DHBV DNA status: Hemospasia through the cervical vein of the ducks was conducted before treatment, at 2 weeks after treatment, at the end of treatment and 1 week after discontinuation respectively. The collected serum samples were stored at $-20\,°$ C. for later determination and comparative analysis, which was undertaken by blot hybridization with Digoxigenin-labeled probe. Plasmid DNA homologous with the probe was doubly diluted and applied on the nitrocelluloose membrane and he color of its hybridization blot was taken as the cretiria in comparasion with hybridization blot color of the test serum for quantitating DHBV DNA in the test serum.

(2) After discontinuation, half of the animals in each group were sacrificed and a small portion of their liver tissue was separated and immobilized in 10% formolite solution for routine HE staining pathological test. The remainders of the tissue were put in cylinders with ice and stored in the lab at $-70°$ C. for extracting the total DNA of the liver tissue, which was detected by Southern blot assay for study on the Ubenimex effects on the replication of DHBV DNA.

(3) In each group, the serum ALT and AST level was determined before treatment, at 2 weeks after therapy, at the end of therapy and 1 week after discontinuation respectively.

Results:

1. DHBV DNA status before therapy, during therapy and after therapy.

In the positive control group and Ubenimex groups of low, medium and high doses, significant or very significant DHBV DNA titer decline occured at the end of therapy, compared with that before therapy: in the Ubenimex of low dose, DHBV DNA titer was also significantly lower at 2 weeks after treatment. The DHBV DNA titer was observed to elevate again at 1 week after discontinuation, and this was shown in Table 1. In the animals infected with low titer DHBV DNA, the DHBV DNA was more likely to lose. For the positive control animals, the eradication rates of DHBV DNA at 2 weeks after therapy and at the end of therapy were 30.77 % and 46.15 % respectively, slightly but unsiginificantly higher than that in the 3 Ubenimex groups ($P<0.05$), as shown in Table 2. It seemed that the degree of DHBV DNA decline and the frequency in loss of DHBV DNA was dose-independent.

TABLE 1

Serum DHBV DNA Titers before and after Therapy (X ± S)

logDH8V-DKA (Pg/m)) % S

| group | cases | before therapy | 2 wks after therapy | 1 mth after therapy | 1 wk after discontinuation |
|---|---|---|---|---|---|
| negative control | 15 | 2.27 ± 1.00 | 2.13 ± 1.02 | 2.47 ± 1.02 | 2.47 ± 1.15 |
| positive control | 13 | 1.69 ± 0.99 | 2.30 ± 1.15 | 0.54 ± 0.50** | 2.48 ± 1.04 |
| Ubenimex (low dose) | 18 | 2.45 ± 1.07 | 1.57 ± 1.30* | 1.17 ± 1.07** | 1.50 ± 1.07* |
| Ubenimex (medium dose) | 18 | 2.31 ± 1.18 | 1.69 ± 1.36 | 1.56 ± 0.86* | 2.00 ± 1.23 |
| Ubenimex (high dose) | 14 | 2.38 ± 1.17 | 1.71 ± 1.03 | 1.36 ± 1.03* | 1.93 ± 1.33 |

Note: "*": $P < 0.05$
"**": $P < 0.01$

Change in DHBV DNA titer before and after therapy of the individual duck in each group was shown in Annex 1~5.

TABLE 2

Eradication Rate of DHBV DNA after Therapy (%)

| group | 2 wks after therapy | 1 mth after therapy | 1 wk after discontinuation |
|---|---|---|---|
| negative control | 0 (0/15) | 0 (0/15) | 0 (0/15) |
| positive control | 30.77 (4/13) | 46.15 (6/13) | 7.69 (1/13) |
| Ubenimex (low dose) | 27.78 (5/18) | 27.78 (5/16) | 16.67 (3/18) |
| Ubenimex (medium dose) | 25.00 (4/16) | 6.25 (1/16) | 12.50 (2/16) |
| Ubenimex (high dose) | 14.29 (2/14) | 21.43 (3/14) | 21.43 (3/14) |

2. Pathological Test of the Liver by HE Staining

Varying degree of vacuolar degeneration and tumofaction of liver cells was found in each group, and infiltration of inflammatory cells in portal area and septum interlobulares occured in some animals. There was no significant difference in the non-specific liver pathological feature between negative control group and the other 4 groups. And the 3 Ubenimex groups were negative for necrosis and hyperplasia of hepocytes.

3. Southern blot assay on DNA extract from the liver tissue

In the groups treated with Aciclovir or Ubenimex the titer of DHBV DNA in the liver tissue commonly decreased, particularly of the relaxed cyclic DNA(RC), super cyclic DNA(SC) and single-stranded DNA(SS).

4. Serum transaminase level before and after treatment

As shown in Table 3 and Table 4, the serum ALT and AST level in all the groups declined to normal in a time-dependant way (ten grown up ducks negative of serum DHBV were tested for the serum ALT and AST level, with the ALT and AST values being <44.47 unit and <49.35 unit). Although the rise of transaminase level was only a transient impact of DHBV infection, there existed very significant difference ($P<0.01$) in serum ALT level at 2 weeks after and at the end of treatment between Ubenimex groups and the negative control group. In contrast, the Aciclovir group did not demonstrate significantly higher ALT level at 2 weeks after and at the end of treatment, compared with the negative control group ($P>0.05$). Moreover, no significant discrepancy in AST level were shown at 2 weeks after treatment among all the groups ($P>0.05$). Whereas, at the end of therapy and 1 week later, AST level of the negative group was significantly lower than that of the other 4 groups.

animal model in study on the Hepatitis B pathology, HBV replication and screening of effective agent against Hepatitis B. In ducklings of 1–3 days old, viremia can persist for a sufficiently long time, without significant loss of HBV DNA. In the light of the above fact, we used the duck as the animal model to study the anti-viral activity of Ubenimex and have provided valuable reference for its clinical therapy of patients with Hepatitis.

As the study showed, the serum DHBV DNA titers had significant decline after 1 month Ubenimex therapy. And in the Ubenimex groups, although DNA elevation occured after discontinuation, the elevated values were not as high as that of the positive group (with Aciclovir treatment), in which DNA titers at 1 week after discontinuation was detected to exceed the pretreatment values. In addition, the anti-viral efficacy of Ubenimex was independent of its dosage, and even 1 month treatment with low dose of Ubenimex demonstrated significant inhibitory activity against HBV.

Liver pathlolgical test and serum ALT test before and after treatment indicated no significant influence of Ubenimex on histological features of the liver. On the other hand, a significant decline in serum ALT and AST level occured in the Ubenimex-treated groups, in comparasion with the 2 control groups, and this suggested that Ubenimex contributed to the improvement of the liver function.

Quantitated by Southern blot assay, the amount of RC DNA, SC DNA and SS DNA in the liver tissue all showed

TABLE 8

Serum ALT level before and after Therapy (U:X ± S)

| group | before therapy | 2 wks after therapy | 1 mth after therapy | 1 wk after discontinuation |
|---|---|---|---|---|
| negative control | 75.59 ± 7.21 | 74.20 ± 7.78 | 55.74 ± 13.87 | 50.58 ± 15.73 |
| positive control | 72.42 ± 11.09 | 69.34 ± 5.21 | 49.59 ± 10.65 | 49.79 ± 17.81 |
| Ubenimex (low dose) | 73.58 ± 8.42 | 63.31 ± 8.52** | 39.77 ± 16.28** | 40.24 ± 12.48* |
| Ubenimex (medium dose) | 70.69 ± 13.24 | 50.98 ± 10.11** | 38.42 ± 21.11** | 38.48 ± 28.79* |
| Ubenimex (high dose) | 76.47 ± 14.56 | 57.58 ± 7.09** | 42.45 ± 8.53** | 42.62 ± 12.97 |

Note: "*": $P < 0.05$
"**": $P < 0.01$

TABLE 4

Serum AST level before and after Therapy (U:X ± S)

| group | before therapy | 2 wks after therapy | 1 mth after therapy | 1 wk after discontinuation |
|---|---|---|---|---|
| negative control | 58.83 ± 10.37 | 68.87 ± 11.06 | 51.24 ± 14.32 | 54.82 ± 25.01 |
| positive control | 71.64 ± 17.06 | 61.74 ± 8.87 | 31.68 ± 3.39* | 48.34 ± 19.61* |
| Ubenimex (low dose) | 74.15 ± 11.46 | 65.79 ± 17.20 | 35.70 ± 18.15* | 42.16 ± 17.06* |
| Ubenimex (medium dose) | 70.02 ± 14.57 | 69.50 ± 11.70 | 35.58 ± 27.80* | 45.56 ± 28.15* |
| Ubenimex (high dose) | 73.70 ± 8.79 | 70.97 ± 11.60 | 43.91 ± 10.46* | 43.58 ± 11.74* |

Note: "*": $P < 0.05$
"**": $P < 0.01$

Dicussion:

Both DHBV and HBV belong to Hepadnavirus, and the DHBV-infected duck becomes increasingly popular as the a decrease at the end of treatment with Ubenimex, and this indicated inhibitory effects of Ubenimex on HBV DNA replication in the liver.

EXAMPLE 2

Effects of Ubenimex On $CCl_4$-induced Liver Damage of Mice

Material:
1. Animals: ICR mice, weighing 18~22 g, half males and half females, provided by the Animal Breeding House of Sichuan Industrial Institute of Antibiotics (SIIA).
2. Drugs: Ubenimex (referred to as BS hereafterin) white powder, batch No.: 94836B, provided by SIIA; Biphenyl dicarboxylate, manufactured by Pilot Plant of Research Institute of Material of Chinese Academy of Medicine Science; $CCl_4$: manufactured by Chongqing South Plant of Chemical Reagent; AR: diluted white plant oil to a 0.1% solution for usage.

Method:
The mice were randomly divided into 5 groups, in 3 of which, Ubenimex of 0.5 mg/kg/day, 0.5 mg/kg/day and 5mg/kg/day was respectively given by the oral route for 7 days; the other 2 groups were negative control (administered with normal saline) and positive control (orally admininstered with Biphenyl dicarboxylate (referred to as BD) of 60 mg/kg/day for 7 days). The mice in the 5 groups were all injected with 0.1% $CCl_4$ 10 ml/kg by the abdominal cavity at 24 hours after the last administration, and were killed by cervical spine breaking. Another 4 hours later, the blood was collected for serum isolation, and serum ALT and AST level was determined by NP automatic biochemical detector. Repeat the above procedure.

Results:
As shown in the following table.

Subject Information: BS group involved 19 males and 4 females, aged from 8~47 years old, with infection course of 11 months~7 years; control group included 16 males and 4 females, aged from 6~60 years old, similar in disease course, etiology and clinical characteristics with those in BS group.

Assay: Elisa was used to determine the antigen and antibody system of Hepatitis B, and HBV-DNA was examined by PCR. Test of serum samples was carried out for these purposes before therapy, at 2 months and 3 months after therapy respectively.

Therapeutical Regimen:
BS group: administered with 30 mg of BS once daily, with a therapeutical course of 90 days.

Control group: 9 cases with Polyporus umbellatus polysaccharose plus virazole therapy; 11 cases inoculated with HB Vaccine, therapeutic course of 3 months.

Results:
1. Eradication rate of serum markers of HBV replication

In BS group, 3 of the 12 BeAg and HBV-DNA positive patients experiend the loss of both HBeAg and HBV-DNA (3/12), in the 11 patients with presence of HBeAg and absence of HBV, HBeAg loss occured in 8 cases (8/11). The frequency in HBeAg loss was 69% (16/23).

In control group, no HBV-DNA loss was found in the 5 HBV-DNA positive patients, and 5 of the 15 cases with presence of HBeAg was found to be HBeAg negative after treatment, with the eradication rate being 33.3% (5/15). In comparasion between BS group and control group, $\mu=2.1634$ and $P<0.05$ indicated significantly higher frequency in HBeAg and HBV-DNA loss for BS group.

Effects of BS on AST, ALT Level in Mice with $CCl_4$- induced Liver Damage (S ± SD)

| group regimen | ALT (U/L) | | AST (U/L) | |
| --- | --- | --- | --- | --- |
| | 1st | 2nd | 1st | 2nd |
| 1 10 NS | 48.75 ± 18.94 | 45.66 ± 21.47 | 147.39 ± 30.36 | 145.48 ± 28.87 |
| 2 10 BS0.05mg/kg/day po × 7 | 36.98 ± 6.45 | 40.18 ± 24.92 | 140.79 ± 22.25 | 163.55 ± 32.17 |
| 3 10 BS0.5mg/kg/day po × 7 | 31.72 ± 10.23 | 29.93 ± 6.73* | 135.73 ± 31.86 | 138.83 ± 31.10 |
| 4 10 BS5.0mg/kg/day po × 7 | 25.26 ± 11.60** | 24.81 ± 8.50** | 143.41 ± 37.60 | 139.64 ± 30.47 |
| 5 10 BD60mg/kg/day po × 7 | 29.69 ± 5.58** | 13.54 ± 2.64** | 160.80 ± 14.09 | 158.81 ± 12.21 |

Note: "*": $0.01 < P < 0.05$, compared with NS group
"**": $P < 0.01$, compard with NS group ALT level elevation was a major indicator of $CCl_4$-induced liver damage in mice, and the above table showed a significant extenuation of ALT activity in the liver damaged mice administered with BS, compared with that in control groups. This effect of Ubenimex was dose-dependant.

CLINICAL APPLICATION OF THE INVENTION

The following clinical therapy with BS furtherly demonstrates the anti-chronic Hepatitis B activity of BS, but is not limited to the details thereof.

Subject Enrollment: subjects involved in the study were HBeAg positive and/or HBV-DNA positive patients hospitalized between Jan. 1993 and Jan. 1994, who had not undergone any anti-viral agent or hormone therapy. Twenty-three of them were in the BS therapy group and the other 20 cases were included in control group. Clinical classification adn diagnosis standard was in conformation with the revised Provisions by National Acadamy Conference on Viral Hepatitis in May. 1990.

2. Liver function (ALT and SB)

In BS group, serum ALT level of the patients before therapy was 51~386$\mu$, and during the first 2 months of treatment, except for an 8 year old child infected through his mother, 22 cases were found to have elevated ALT level in varying degree, among whom 15 cases showed a fall to the normal at 3 months after therapy, with the normalization rate being 65.2% Moreover, the SB levels of BS group ranged from 4 $\mu$mol/L to 17.1 $\mu$mol/L before therapy, and after therapy, 22 cases maintained the normal level except for one patient whose SB level increased to 19.1 $\mu$mol/L but fell to normal after treatment.

In control group, all the 20 cases were abnormal in ALT level before therapy, and 12 of them were found to have ALT level normalization after therapy, with the normalization rate of 60%. $\mu=0.035$ and $P<0.05$ was considered to be no significant difference as compared with BS group. A slight elevation in SB level was found in some cases of the control group, and this was followed by normalization after liver-care treatment.

Discussion:

A comparative study on the anti-chronic persistent Hepatitis B activity of Ubenimex was iperformed in 23 BS-treated patients, with Polyporus umbellatus polysaccharose plus Virazole therapy as control in 20 cases. As the result showed, BS had higher efficacy against HBV than Polyporus umbellatus polysaccharose, with convenient administration route and no significant side effect.

In summary, the above laboratory research and clinical study indicates that Ubenimex possesses good efficacy against viral Hepatitis, particularly against viral Hepatitis B.

Annex 1. DHBV DNA Titers before and after Therapy (negative group)

| No. | before therapy | 2 wks after therapy | 1 mth after therapy | 1 wk after discon. |
|---|---|---|---|---|
| 25  | ++   | ++   | +++  | ++++ |
| 35  | +++  | +    | ++   | +++  |
| 60  | ++   | +    | ++   | +    |
| 81  | ++   | ++   | ++++ | +    |
| 82  | +++  | +++  | +++  | +++  |
| 90  | +    | +    | +++  | ++++ |
| 121 | +    | +++  | +++  | +++  |
| 122 | ++++ | ++++ | ++++ | ++++ |
| 135 | +++  | +    | ++   | +    |
| 138 | +    | ++   | +    | +    |
| 174 | +    | ++   | +++  | +++  |
| 175 | +++  | +++  | ++++ | +++  |
| 198 | ++++ | ++++ | ++++ | +++  |
| 208 | ++   | +    | +    | +    |
| 209 | ++   | ++   | +++  | ++   |

Annex 2. DHBV DNA Titers before and after Therapy (positive group)

| No | before therapy | 2 wks after therapy | 1 mth after therapy | 1 wk after discon. |
|---|---|---|---|---|
| 13  | +    | +    | −    | ++++ |
| 15  | ++++ | ++   | +    | ++   |
| 54  | +    | +++  | +    | +    |
| 78  | +    | +++  | +    | ++   |
| 94  | +    | ++   | −    | +++  |
| 95  | ++   | +    | −    | ++   |
| 115 | +    | −    | −    | ++   |
| 134 | +    | −    | +    | +++  |
| 136 | +    | −    | −    | +++  |
| 158 | ++   | +    | +    | ++++ |
| 201 | +++  | ++   | +    | +++  |
| 199 | +    | −    | −    | −    |
| 214 | +++  | +++  | +    | +++  |

Annex 3. DHBV DNA Titers before and after Therapy (BS group of low dose)

| No | before therapy | 2 wks after therapy | 1 mth after therapy | 1 wk after discon. |
|---|---|---|---|---|
| 5   | +    | −    | −    | −    |
| 9   | ++   | +++  | +    | ++   |
| 10  | +    | −    | +    | +    |
| 39  | ++   | ++   | ++++ | +    |
| 80  | ++++ | +++  | ++   | ++   |
| 98  | ++++ | ++++ | +    | +++  |
| 116 | +    | −    | −    | −    |
| 117 | ++   | +    | +    | +    |
| 118 | ++++ | +    | ++   | −    |
| 125 | ++   | −    | −    | +    |
| 131 | +++  | +++  | +    | +++  |
| 139 | ++   | +    | +    | ++   |
| 170 | ++++ | +++  | ++++ | ++++ |
| 193 | +++  | +    | +    | +    |
| 197 | +++  | ++   | ++   | +    |
| 210 | ++   | ++   | −    | ++   |
| 226 | +    | −    | −    | +    |
| 230 | ++   | +++  | +    | ++   |

Annex 4. DHBV DNA Titers before and after Therapy (Bs group of medium dose)

| No | before therapy | 2 wks after therapy | 1 mth after therapy | 1 wk after discon. |
|---|---|---|---|---|
| 20  | +++  | +++  | ++   | ++++ |
| 38  | +    | ++   | +    | ++   |
| 63  | +++  | +    | −    | +    |
| 78  | ++++ | +    | +    | ++   |
| 79  | +    | +    | +    | −    |
| 96  | +    | −    | +    | +    |
| 101 | +    | +    | +    | −    |
| 113 | ++   | −    | +    | +    |
| 129 | +++  | ++++ | ++   | +++  |
| 132 | ++   | +++  | ++   | +    |
| 140 | +++  | +++  | +++  | +++  |
| 152 | +    | −    | ++   | ++   |
| 177 | ++++ | ++   | +    | +++  |
| 203 | ++++ | ++   | +++  | +++  |
| 205 | +++  | +++  | +++  | ++++ |
| 225 | +    | −    | +    | ++   |

Annex 5. DHBV DNA Titers before and after Therapy (BS group of high dose)

| No | before therapy | 2 wks after therapy | 1 mth after therapy | 1 wk after discon. |
|---|---|---|---|---|
| 17  | ++++ | ++   | ++   | +    |
| 31  | ++++ | ++   | +    | ++   |
| 46  | +    | +    | ++   | ++   |
| 66  | ++   | +++  | +    | −    |
| 86  | ++++ | +++  | +++  | ++++ |
| 100 | ++   | +++  | ++   | ++   |
| 106 | +    | +    | +    | ++   |
| 150 | +    | +    | +    | ++   |
| 163 | +++  | +++  | +++  | ++++ |
| 169 | +    | −    | −    | −    |
| 191 | ++   | ++   | ++   | ++   |
| 195 | ++   | +    | −    | ++++ |
| 207 | ++++ | ++   | +    | ++   |
| 248 | +    | −    | −    | −    |

Note: "++++": 10,000pg
"+++": 1,000pg
"++": 100pg
"+": 10pg
"−": <1pg

We claim:

1. A method for the treatment of viral hepatitis in an animal, comprising administering to said animal a therapeutically effective amount of ubenimex or salt thereof.

2. The method of claim 1, wherein said animal is a mammal.

3. The method of claim 2, wherein said mammal is human.

4. The method of claim 1, wherein said viral hepatitis is chronical hepatitis B.

5. The method of claim 1, wherein said ubenimex or salt thereof is administered parenterally.

6. The method of claim 1, wherein said ubenimex or salt thereof is administered orally.

7. The method of claim 5, wherein said ubenimex or salt thereof is administered intramuscularly, intravenously, intraperitoneally or subcutaneously.

8. A method for treating viral hepatitis in an animal, comprising administering to said animal a pharmaceutical composition comprising a therapeutically effective amount of ubenimex or salt thereof.

9. The method of claim 8, wherein said composition further comprises pharmaceutically acceptable adjuvant and excipient.

10. The method of claim 8, wherein said composition further comprises one or more other anti-viral hepatitis agents.

11. The method of claim 8, wherein said pharmaceutical composition is administered orally.

12. The method of claim 8, wherein said pharmaceutical composition is administered intravenously, intramuscularly, intraperitoneally or subcutaneously.

13. The method of claim 8, wherein said animal suffers from chronical hepatitis B.

14. The method of claim 8, wherein said animal is a mammal.

15. The method of claim 14, wherein said mammal is human.

* * * * *